US011101027B2

(12) United States Patent
Cline et al.

(10) Patent No.: US 11,101,027 B2
(45) Date of Patent: *Aug. 24, 2021

(54) MESSAGING PROTOCOL

(71) Applicant: CERNER INNOVATION, INC., Kansas City, KS (US)

(72) Inventors: Christopher Dillard Cline, Smithville, MO (US); Aravind R. Mereddi, Overland Park, KS (US); Joel Robert Norton, Overland Park, KS (US); Scott Gordon Siebers, Leawood, KS (US)

( * ) Notice: Subject to any disclaimer, the term of this patent is extended or adjusted under 35 U.S.C. 154(b) by 145 days.

This patent is subject to a terminal disclaimer.

(21) Appl. No.: 16/585,457

(22) Filed: Sep. 27, 2019

(65) Prior Publication Data
US 2020/0027538 A1 Jan. 23, 2020

Related U.S. Application Data

(63) Continuation-in-part of application No. 15/437,857, filed on Feb. 21, 2017, now Pat. No. 10,453,565.

(60) Provisional application No. 62/439,543, filed on Dec. 28, 2016.

(51) Int. Cl.
| H04L 29/08 | (2006.01) |
| G16H 15/00 | (2018.01) |
| H04L 12/58 | (2006.01) |
| G16H 10/60 | (2018.01) |
| H04L 29/06 | (2006.01) |
| G06F 21/62 | (2013.01) |

(52) U.S. Cl.
CPC ......... *G16H 15/00* (2018.01); *G06F 21/6245* (2013.01); *G16H 10/60* (2018.01); *H04L 51/28* (2013.01); *H04L 63/04* (2013.01); *H04L 67/12* (2013.01)

(58) Field of Classification Search
CPC ........ G16H 10/60; G16H 40/67; G16H 30/20; H04W 4/00; H04W 4/14; A61B 8/565; H04L 29/06; H04L 69/08
See application file for complete search history.

(56) References Cited

U.S. PATENT DOCUMENTS

| 2012/0254349 A1 | 10/2012 | Quigley et al. |
| 2014/0114706 A1* | 4/2014 | Blakely .................. G06Q 10/02 705/5 |
| 2018/0181715 A1 | 6/2018 | Cline et al. |
| 2019/0043615 A1* | 2/2019 | Subbarao ............... G16H 20/13 |

OTHER PUBLICATIONS

First Action Interview received for U.S. Appl. No. 15/437,857, dated Feb. 7, 2019, 7 pages.
Notice of Allowance received for U.S. Appl. No. 15/437,857, dated Jun. 12, 2019, 5 pages.
Pre-Interview First Office Action received for U.S. Appl. No. 15/437,857, dated Oct. 24, 2018, 6 pages.

* cited by examiner

*Primary Examiner* — Hitesh Patel (57) ABSTRACT

Systems and methods provide for implementation of a messaging protocol that provides security necessary for clinical messaging while also providing scalability needed to properly function within a clinical setting. The messaging protocol provides for federation of messages across messaging domains with a direct target address or via a role or group endpoint address that resolves to one or more target addresses. The messaging protocol also provides the ability to include content other than text in messages.

18 Claims, 4 Drawing Sheets

MESSAGING PROTOCOL

CROSS-REFERENCE TO RELATED APPLICATIONS

This application is a continuation-in-part that claims the benefit of U.S. patent application Ser. No. 15/437,857, filed Feb. 21, 2017, entitled "Messaging Protocol," now issued as U.S. Pat. No. 10,453,565, which claims the benefit of U.S. Provisional Patent Application No. 62/439,543, filed Dec. 28, 2016, entitled "Messaging Protocol," the disclosure of both of which are incorporated herein by reference in their entirety.

BACKGROUND

Messaging of clinically relevant data is a challenge for many reasons. Initially, security is a concern due to heightened security regulations regarding clinical data. Additionally, scalability (the ability to handle a growing amount of work) is a challenge for typical messaging systems. A system that is scalable and equipped with the proper security measures is desirable to be able to target a clinical workspace messaging environment.

SUMMARY

Embodiments of the present invention relate to, among other things, a messaging protocol for a clinical workspace. The messaging protocol of the present invention provides for secure communication even over disparate messaging domains. The messaging protocol is scalable over disparate messaging domains and can communicate messaging transmissions across messaging domains, even when the target endpoint address is unknown.

Accordingly, in one aspect, a computer system comprising: one or more processors; and one or more computer storage media storing computer-useable instructions that, when used by the one or more processors, cause the one or more processors to detect a request to transmit a message to a destination where a target endpoint address is unknown, wherein the destination is within a separate domain; determine whether the destination is associated with a role; upon determining the destination is associated with a role, identify an intended target associated with the role; generate a transmission for the intended target; and electronically communicate the transmission to the intended target within the separate domain.

In another embodiment, an aspect is directed to a computer-implemented method. The method includes detecting a request to transmit a message to a destination where a target endpoint address is unknown, wherein the destination is within a separate domain; determining whether the destination is associated with a role; upon determining the destination is associated with a role, identifying an intended target associated with the role; generating a transmission for the intended target; and electronically communicating the transmission to the intended target within the separate domain.

A further embodiment is directed to one or more computer storage media storing computer-useable instructions that, when executed by a computing device, cause the computing device to perform operations. The operations include detecting a request from a source device within a first domain to transmit a message to a plurality of destinations within a second domain where a target endpoint address is unknown for each of the plurality of destinations; identifying one or more intended targets associated with the plurality of destinations, wherein the one or more intended targets are discoverable within a network including the second domain; generating a transmission for the one or more intended targets; electronically communicating the transmission to the one or more intended targets within the second domain; receiving a plurality of responses from the one or more intended targets; electronically communicating each of a device acknowledgement and a read acknowledgement to the source device, wherein only one device acknowledgement and one read acknowledgement are communicated to the source device; and electronically communicating a response from each of the one or more intended targets to the source device. This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The present invention is described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention provide a messaging protocol with necessary security and scalability measures for clinical workflows. The messaging protocol provides the ability to send messages, notifications, alerts, etc., including clinical relevance data across disparate messaging domains with necessary security.

Figure 1:
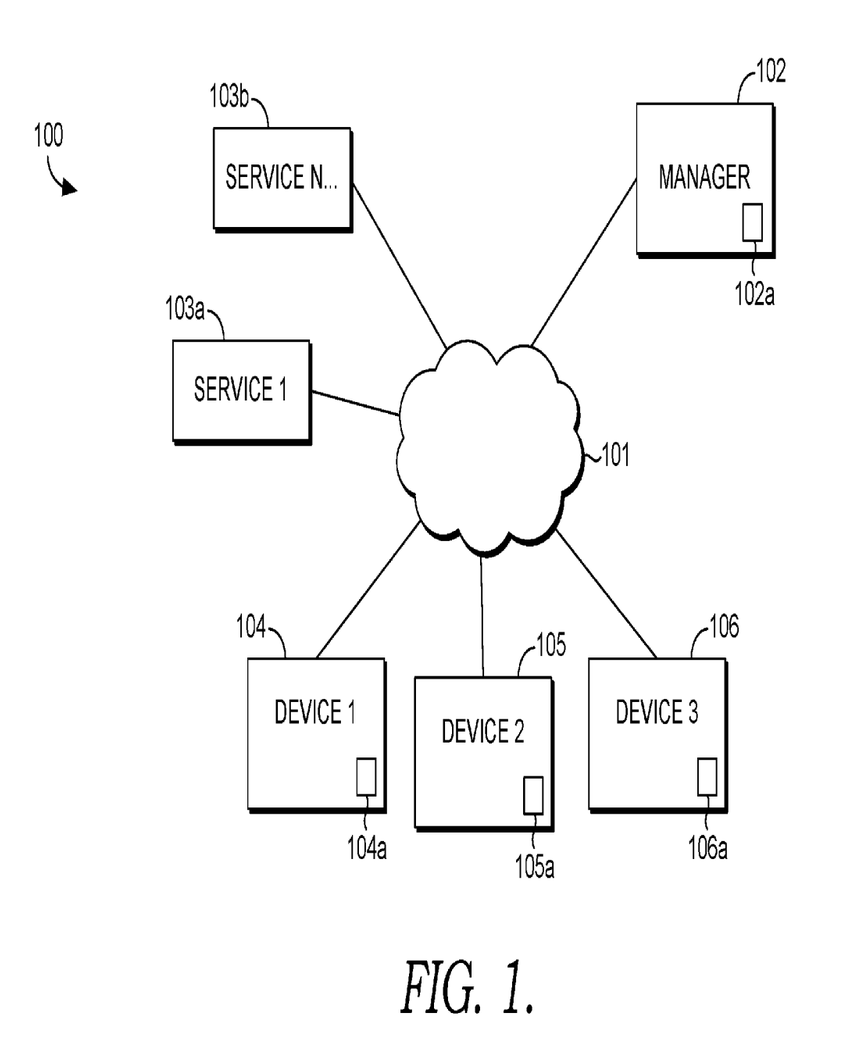
FIG. 1 is a block diagram illustrating an exemplary computing environment in accordance with some implementations of the present disclosure.

An exemplary computing environment suitable for use in implementing embodiments of the present invention is described below. FIG. 1 is an exemplary computing environment (e.g., clinical messaging environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include mobile phones, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 may comprise a computing device in the form of a control server (not shown). Exemplary components of the control server comprise a processing unit, internal system memory, and a suitable system bus for coupling various system components, including a data store, with the control server. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus. The manager 102 may be embodied within the control server.

The control server typically includes therein, or has access to, a variety of non-transitory computer-readable media. Computer-readable media can be any available media that might be accessed by control server, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server and/or manager 102 might operate in a computer network 101 using logical connections to one or more devices 104, 105, 106, and 107. Devices 104, 105, 106, and 107 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The present invention may also apply to non-clinician staff working in a medical or research environment, such as administration and operations personnel. The devices 104, 105, 106, and 107 might also be physically located in nontraditional medical care environments so that the entire healthcare community might be capable of integration on the network. The devices 104, 105, 106, and 107 might be personal computers, servers, routers, network PCs, peer devices, other common network nodes, or the like and might comprise some or all of the elements described above in relation to the manager 102. The devices can be personal digital assistants, mobile phones, cameras, or other like devices.

Computer networks 101 comprise local area networks (LANs) and/or wide area networks (WANs). Such networking environments are commonplace in offices, enterprise-wide computer networks, intranets, and the Internet. When utilized in a WAN networking environment, the control server might comprise a modem or other means for establishing communications over the WAN, such as the Internet. In a networking environment, program modules or portions thereof might be stored in association with the control server or any of the devices 104, 105, 106, and 107. For example, various application programs may reside on the memory associated with any one or more of the devices 104, 105, 106, and 107. It will be appreciated by those of ordinary skill in the art that the network connections shown are exemplary and other means of establishing a communications link between the computers (e.g., manager 102 and devices 104, 105, 106, and 107) might be utilized.

In operation, an organization might enter commands and information into the control server or manager 102 or convey the commands and information to the control server or manager 102 via one or more of the devices 104, 105, 106, and 107 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the manager 102. In addition to a monitor, the manager 102 and/or devices 104, 105, 106, and 107 might comprise other peripheral output devices, such as speakers and a printer.

The computing environment 100 may also include one or more services 103a and 103b. The services may be provided within a protocol stack and added as necessary for scalability of the system 100.

Although many other internal components of the manager 102 and the devices 104, 105, and 106 are not shown, such components and their interconnection are well known. Accordingly, additional details concerning the internal construction of the manager 102 and the devices 104, 105, and 106 are not further disclosed herein.

Figure 2:
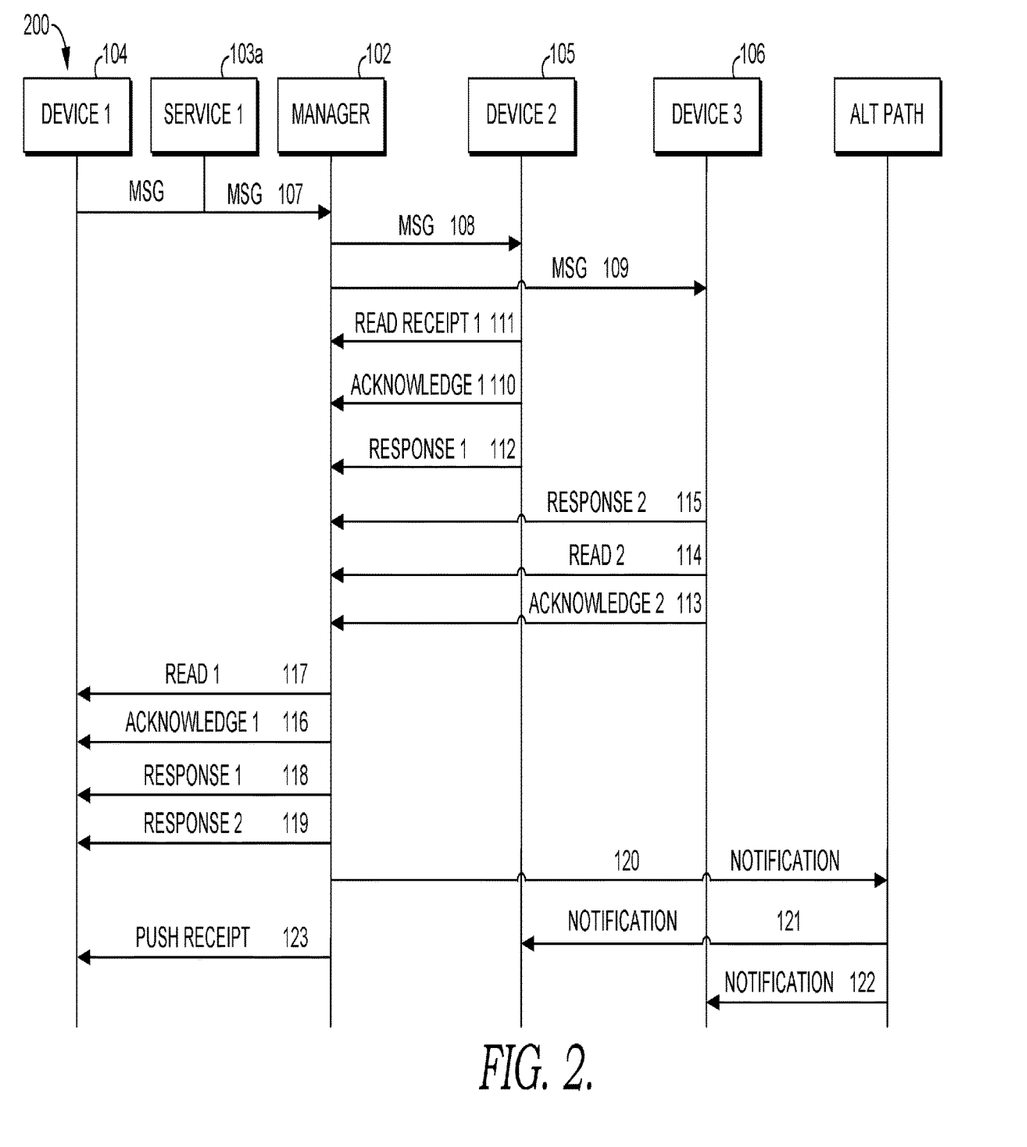
FIG. 2 is a flow diagram illustrating an exemplary method for implementation of the messaging protocol in accordance with some implementations of the present disclosure.

Turning now to FIG. 2, an exemplary workflow is illustrated implementing the clinical messaging protocol of the present invention. Initially, the devices 104, 105, 106, and 107 of FIG. 1 are shown along with the manager 102, and service 1 103a. A device, such as device 104 requests to send a message to an endpoint. Messages, as used herein, refer generally to an exchange of an individual textual payload between two or more participants (devices). The present system may be utilized for the transmission of notifications and alerts in addition to messages. Notifications and alerts, as used herein, refer generally to transmissions that are generated from the source system. While the system can handle any of the above-mentioned transmissions, messages are depicted in exemplary FIG. 2.

The manager 102 is meant to represent the messaging protocol of the present invention. In embodiments, the manager 102 consists of both a JavaScript Object Notation (JSON) serialized transport and application layer protocol. It may sit atop a TCP websocket connection and provide messaging between an endpoint and a service. An endpoint, as used herein, refers generally to a physical instance of an application running on a device for which a user can generate a session.

An endpoint is an entity that is network addressable and can be communicated with using the messaging protocol. The messaging protocol may leverage a mailbox to domain style addressing scheme. This will define an endpoint at which users, groups, and services can receive messages. The structure of the addressing scheme is similar to the following: user@domain; group@domain; and service@domain. Domains may be defined globally across all clients and the parent domain may be owned by a first entity. Sub-domains may exist and may be controlled within an individual organization to separate sub-groups of delivery endpoints into logical groupings as necessary.

The endpoints are uniquely identifiable by an address. The messaging protocol addresses may be a string in an ordered sequence of three parts:

Endpoint Identifier;

Domain—may be a fully qualified messaging protocol domain;

Resource—an optional resource that identifies the device or location of endpoint; and Human Readable Name—an optional name that describes the endpoint.

By allowing the first entity to own the parent domain registrations, rules can be defined that will allow for federation between various client organizations or domains. Federation within a client organization may be controlled primarily through the use of subdomains unless an organization requests multiple parent domains. A messaging domain may be a group of devices, users, and services on a network that implement the messaging protocol. A domain may be referred to by its name. A messaging domain may also serve as a boundary for a facility or organization. To provide federation between messaging domains, components may be in place in those domains that follow a pre-defined protocol. Applications, for instance, may be present on devices that use the messaging protocol. Exemplary applications may be seen in FIG. 1 as applications 104a, 105a, 106a, and 107a.

A domain lookup table may be developed through a series of parent-child relationships where an individual messaging service shall be able to play the part of either a parent or child node. The instance of the service may be responsible for knowing about all local domains to itself and its children. Should a request for delivery be made to this instance for a domain that it is unfamiliar with, the request may be delivered to its parent for further identification. The ultimate parent service may reside with the first entity and have full knowledge of the parent domain routing tables. Should a parent messaging service not be able to make delivery to either a parent domain, subdomain, or individual mailbox, error handling routines may be enacted for acknowledgement back to the originator.

Domain hierarchy is an organization of domains into parent-child relationships. A parent domain is a domain directly superior to one or more child domains in the hierarchy. A child can have at most one parent domain. An organization typically has only one highest level parent domain. A child domain can also be a parent of one or more child domains. Child domains that share the same parent are sibling domains of one another.

Routing tables may also be present in the manager 102 with entries that map domains to connection endpoints. These can be configured manually or auto-populated by building discovery mechanisms.

The manager 102 can be used to connect physically distinct locations such as hospitals, clinical laboratories, other healthcare related environments, and the like. The manager 102 can interact with systems housed at any of the associated physical locations, provided that a connection exists between the manager 102 and the system(s) housed at any of the physical locations. Once a user has been linked with a system at any one of the associated locations, the system(s) at associated locations separate from the originally-linked location can recognize and establish a session for the user at the separate, non-originating, associated location.

The associated systems (i.e., systems that are associated with the manager 102) can recognize a user that has been previously linked with a separate system. Specifically, when a present system recognizes that a user has been previously linked to a separate associated system, and that the user has not been linked to the present system, the present system will allow the user to link to it. This can be done by the system automatically, the manager, or through input of the user. Once the user has been linked to the present system, the present system as well as the separate associated system can recognize the user's presence (or the device's presence) at the present system. Additionally, the originally-linked system (separate associated system) can recognize the user's presence at any associated location separate from the originally linked-location. Once the user/user device has been detected, the originally-linked location can automatically link the user/user device to the associated location. The originally-linked system can then send messages to the user at the associated location through the system of the associated location.

In a further embodiment, the manager 102, in addition to the individual systems themselves, can detect when a user is physically located at an associated location at which the user has not previously been linked. The manager 102 can link the user to the system at the associated location at which the user has not previously been linked. The manager 102 can coordinate messages between the originally-linked location and the newly linked location, allowing the user to receive messages from another system. For instance, by way of example, assume a message is to be designated to a user as an intended target. The manager 102 can, initially, search the system where the target user was originally linked. The target user may or may not be present within the facility controlled by the system where the target user was originally linked. In the event the target user is present, the message is communicated, as described hereinafter. In the event the target user is not present within the facility controlled by the system where the target user was originally linked, the manager 102 can recognize that the user is not present at the originally linked system. Upon identifying that the target user is not present within the facility controlled by the system where the target user was originally linked, the manager 102 can search other associated systems for the presence of the target user. The manager 102 can search any associated system having a connection with the manager 102 (i.e., any system registered with the manager). Once the target user is discovered at an associated system, the manager 102 can send the message to the intended target user at the associated system location, utilizing the separate system at the associated system location.

In an additional embodiment, a user device is used to automatically connect the user to the systems. Once the user has been linked to a system, the user's device will automatically detect and link to separate associated systems. Once the user's device has linked to the separate associated system, the separate associated system can detect that the user has been linked to an original system and can then notify the original system of the user's new location at the separate associated system. The original system can then reroute messages meant for the user to the separate associated system for delivery to the user.

Returning now to FIG. 2, a message is communicated from device 104 to service 103a. There may be any number of services (as shown in FIG. 1) that all route to a common service manager 102. The manager 102 determines an optimal path to the endpoints. Recall from the discussion above that the messaging protocol federates messages outside of a facility where a target endpoint address is unknown. For example, a user in Facility 1 may need to communicate with a user in Facility 2 and not know their address (e.g., send a message to the on-call cardiologist at Facility 2). The messaging protocol is still able to communicate the message due to the federation implementations discussed above.

When an optimal path is available, the manager 102 communicates the message transmission via transmission 108 to the device 105. In this example, the message was also intended for another target (device 106) so the manager 102 communicates the message to the device 106 via transmission 109. When the messages are confirmed delivered, the messaging protocol has reliability guarantees built in that provide certain measures for confirming delivery status. A device-level acknowledgement indicates that the message has been reliably delivered to the intended device. A user-level acknowledgement (e.g., read receipt) indicates that the message content has been presented on the device.

The messaging protocol is configured to receive, at the manager 102, device-level acknowledgements and user-level acknowledgements from each target that received a message. As shown in FIG. 2, the manager 102 receives a read receipt 111 (user-level acknowledgement indicating that content of message 108 was displayed) and an acknowledgement 110 (device-level acknowledgement indicating the message 108 was delivered to the device). The same type of acknowledgements have been received at manager 102 from device 106 (shown as read receipt 114 and acknowledgement 113 in FIG. 2).

Additionally, when appropriate, responses may also be received at manager 102. Responses from any target device may be received at the manager 102. As shown in FIG. 2, response 112 is received from device 105 and response 115 is received from device 106.

Once an initial device-level acknowledgement (such as acknowledgement 110) and a user-level acknowledgement (such as read receipt 111) are received at manager 102, the manager 102 communicates the first received acknowledgements back to the source device (i.e., device 104). This is depicted in transmission 116 and 117 of FIG. 2. While only the first received acknowledgements are communicated to the source device 104, every single response that is received by the manager 102 is forwarded on to the source device 104 as shown in transmissions 118 and 119.

In embodiments, when an optimal path is not available, the manager 102 identifies an alternate path that may be used. Because clinical information is included in the messages discussed herein, the actual payload itself is not communicated to the alternate path. Rather, a notification of the message is communicated via transmission 120. Thus, a notification 121 of the message, not the message itself may be routed through an alternate path. The notification 121 is then sent to the target device 107. Optionally, a push receipt 122 may be communicated from the manager 102 to the source device 104 to notify the source device 104 that an alternate path was used.

In embodiments, the manager 102 has the ability to update content using the messaging protocol. Prior clinical messaging or alerting systems do not have the capability to update content of the messages transmitted. Because the current messaging protocol can be expanded with as many services as are necessary, updates to the content are endless. As an example, an alert that is communicated may be taken care of by a recipient of the alert. This alert would need to be updated so that other recipients are aware that the alert no longer needs attention. The messaging protocol is configured to update the alert using the original message and original identifier and including updated content. The information with which to update the alert may be triggered from an electronic medical record, a device, etc. For instance, an alert generated to dispense medications to a patient may be updated when documentation of administration of the medication is entered in the EMR of the patient.

The manager 102 may be configured with a timer 102a. The timer 102a may be useful to identify when messages have not been reliably delivered. For instance, the manager 102 may utilize the timer 102a to determine when to seek out an alternate path. Upon expiration of a predetermined time period, the manager 102 may evaluate alternate paths if no device-level acknowledgement is received. The same may be applied to user-level acknowledgements. If a message is delivered (e.g., the device-level acknowledgement has been received) and no user-level acknowledgement is received within a predetermined time period, the manager 102 may escalate the message to additional targets.

The manager 102 can further use the timer 102a to delay or expedite messages. For instance, the manager 102 can detect the presence or absence of delay criteria, to determine whether or not to delay or expedite the message. Delay criteria may comprise presence information, availability information, etc. For example, delay criteria is present if the presence information indicated that the intended target was logged off, not in the clinical facility, scheduled for surgery, or the like (e.g., not present/available to respond to a message). The timer 102a can be used to delay the message for a predetermined amount of time based on the presence of the delay criteria. Additionally, the intended target could receive the message and then choose to be reminded of the message after a set amount of time. The manager 102 could re-send the message to the intended target at the newly designated time.

Delayed messaging or reminder-type settings may only be available for certain messages. For instance, some messages relate to critical issues and need urgent attention such that delaying the message or offering a reminder option is not practical. Messages can be associated with a delivery identifier indicating availability for delayed delivery or reminder options. Alternatively, messages can be associated with a delivery identifier indicating the message is not available for delayed delivery or reminder options. The manager 102 can detect the delivery identifier and provide appropriate options based thereon. For instance, if a delivery identifier is present that indicates a message is not eligible for delay, regardless of the presence of delay criteria, the message will not be delayed and alternative delivery paths can be identified, as discussed herein. Alternatively, if a delivery identifier is present that indicates a message is eligible for delay (or, in other embodiments, no delivery identifier is present at all), the message can be delayed if there is also delay criteria present. Thus, if delay criteria is not present, delaying the message or providing a reminder option is not triggered. If delay criteria is present, delaying the message or providing the reminder option may be triggered if a delivery identifier indicates that delay or reminders are available (i.e., a delivery identifier actively indicates availability of delay or reminder options or a delivery identifier prohibiting delaying the message or offering reminder options is not present at all).

In view of the above, the manager 102 can also escalate any urgent messages (i.e., messages that are not available for delayed delivery or reminder options) not acted on within a predetermined period of time, delay delivery of a message in prescribed delay situations (e.g., delay criteria present and a delivery identifier that does not prohibit a delay), provide reminders to users upon request by the user or inaction of the user, and the like.

Additionally, the manager 102 can iteratively monitor criteria related to the delay or reminder options for a message. For instance, the manager 102 can delay a message until it detects a change in, for instance, presence information indicating the absence of delay criteria. This iterative monitoring by the manager 102 can be performed at predetermined time intervals. Varying time intervals may be configured for different messages depending on the clinical nature of the message. For instance, a medication message may be eligible for delay, but only up to a certain threshold (e.g., can delay up to one hour but no longer). In those situations, monitoring may be performed more frequently given the smaller delay window compared to instances where a large delay window may be present (e.g., a message indicating a refill is due in one week for a patient may be delayed up to, for example, 5 days and, as such, the manager 102 can monitor less frequently for a change in delay criteria).

Additionally, the manager 102 can detect factors in clinically relevant information which require that the message be delayed or expedited, such as a time requirement for a particular medication, or a delay based on a medication having previously been administered. The clinically relevant information may be accessed from, for example, one or more electronic medical records. The manager 102 can intelligently, without user interaction, identify when it is appropriate to delay a message. In some embodiments, the manager intelligently, without user interaction and without the benefit of a delivery identifier, determines that a message can be delayed, escalated, or provided as a reminder. In embodiments, the intelligent discerning of the manager 102 is provided due to access to clinical information from, for instance, an electronic health record of an individual. For instance, a transmission related to a coding event may be identified by the manager 102 as ineligible for delay without the benefit of a delivery identifier indicating such non-eligibility. Alternatively, a transmission related to a urinalysis result for an individual may be determined, automatically by the manager 102, to be eligible for a delay of a predetermined time period. The manager 102 may learn how to configure the delay time periods based on previously-delayed transmissions.

In addition to presence, proximity determinations may also be utilized by the protocol. For instance, a clinician closest to (in physical proximity) a situation may be notified in addition to an intended recipient. The services supporting the manager 102 can identify proximity information and route to the clinician that is nearest a situation in the case of alerts. Sensors may be utilized to track locations of individuals such that distances between individuals and a target location can be compared to identify the individual in the closest proximity to the target location.

Because of the scalability of the messaging protocol, messages may include various content that was not previously possible to include in messages. For instance, videos, images, wave forms, and the like may all be communicated using the present messaging protocol.

By way of example, assume that Kristen logs into her application (configured to communicate via the messaging protocol) and claims a role of Internal Medicine—Green team. Patient A is Kristen's patient and is intubated in the ER. After claiming her role in the green team group, Kristen may receive a text from Dave, charge nurse, stating "Are you here?" Kristen replies with a quick message of "yes, anything new." Dave, reply texts, "New ER admit, Patient A, MVA, unstable and headed to surgery, they need you." Kristen texts back "on my way." Kristen knows she won't be available for some time due to going into surgery so she transfers her roles to Joseph, Md. Clinical information was able to be sent via text because of the security measures provided in the messaging protocol. Additionally, messages are routed to Kristen because of her claiming the role of Internal Medicine—Green team. Thus, senders do not need to know Kristen's name, her number, or any other endpoint information. They can select a role and the message will be transmitted accordingly.

Alternatively, users, such as Kristen in the above example, can forward messages directed to them to another user(s) without the use of roles. For instance, assume that Kristen is not associated with any roles but she desires to forward messages directed to her to another user (e.g., Joseph) for a specific time period. Kristen can do that using the present protocol. Kristen could further forward any messages sent directly to her (i.e., not a role) to a role rather than a user. Thus, the present protocol can transfer/forward messages from, for instance, role-to-role (e.g., a user transfers a role to another user), user-to-role (e.g., a user transfers messages sent directly to them to a role), role-to-user (e.g., a user associated with a role transfers messages sent to the role to a specific user), and user-to-user (e.g., a user can transfer messages sent directly to them to another user without the use of roles).

Alternatively, upon receiving additional messages, Kristen could select a reminder option (when available) provided by the manager 102 knowing that she will be available in one hour. The manager 102 could resend the additional message(s) to Kristen after the one hour (or any other predetermined time period) had passed. In a further alternative, the manager 102 could detect Kristen's unavailability through detection of delay criteria and determine to delay the message to Kristen, when appropriate (i.e., a delivery identifier prohibiting the delay of a message is not present).

By way of another example, Kristen's association with the system at Hospital A allows her to automatically associate with the system at Hospital B, an affiliated hospital. When the system at Hospital B recognizes Kristen's physical presence, it automatically associates her with the Hospital B system. Because Hospital A and Hospital B are associated with one another or the manager 102, Hospital A can communicate with Kristen through Hospital B's system.

Figure 3:
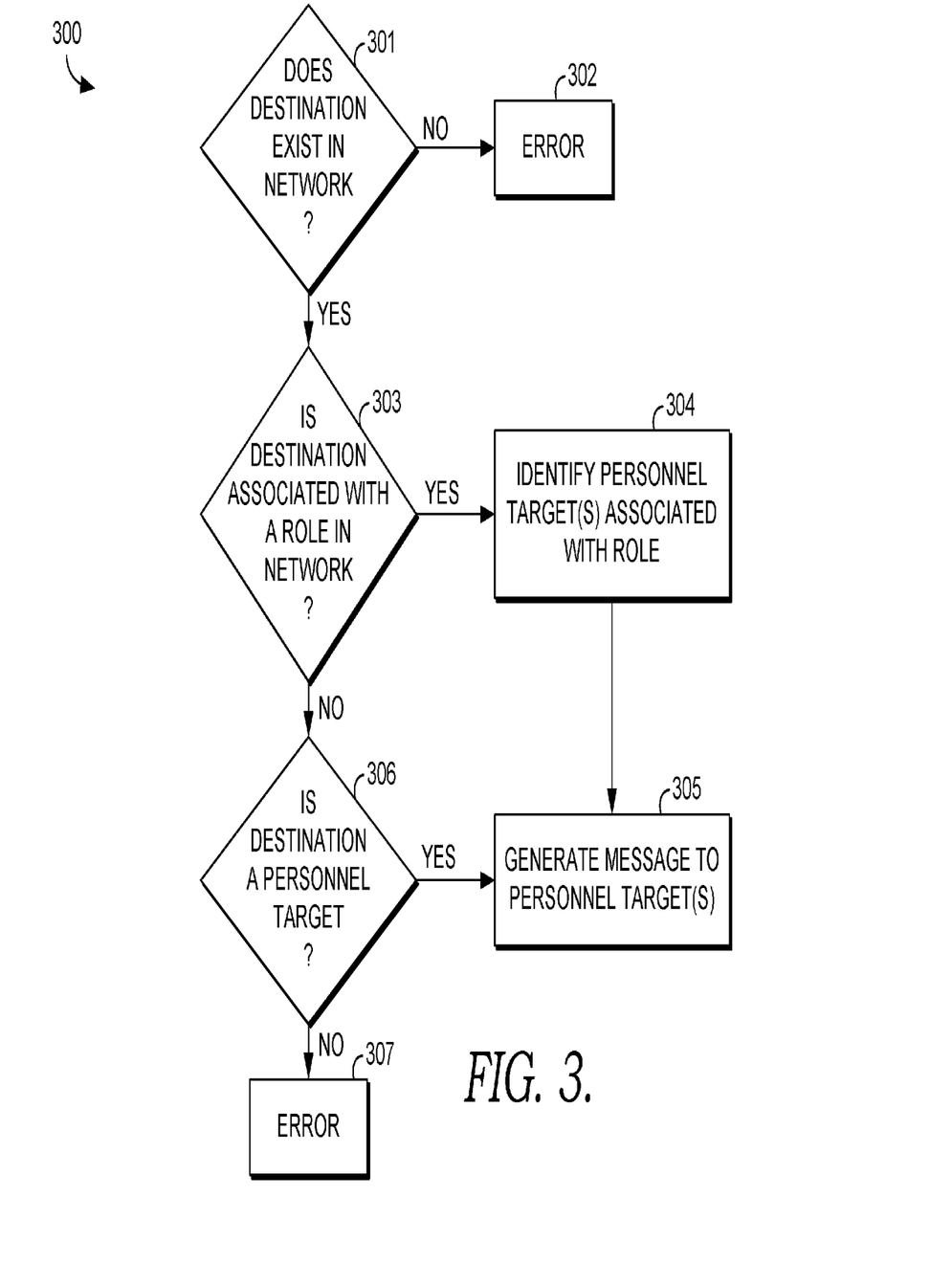
FIG. 3 is a flow diagram illustrating an exemplary method for implementation of the messaging protocol in accordance with some implementations of the present disclosure.

Turning now to FIG. 3, a flowchart is provided of an exemplary method 300 in accordance with embodiments of the present invention. Initially, at block 301, the messaging protocol determines whether the destination exists in the network. As described above, a parent domain may evaluate message destinations. If the destination does not exist within the network, an error is generated at block 302. If the destination does exist within the network, the messaging protocol determines, at block 303, whether the destination is associated with a role/group in the network.

Additionally, as a further embodiment, the roles/groups can be dynamically resolved by the manager 102 based on multiple external factors. For example, the manager 102 may detect that a user travels to a particular location of a hospital (e.g., area 2 North). Once the manager 102 has detected the user's presence at this particular location, the manager can add the user to the group 2 North.

In a further embodiment, the manager 102 can use an external factor such as clinically relevant information to dynamically create or terminate roles/groups. As one example, the manager 102 may detect, through access to electronic medical records, that a particular patient has been admitted to the emergency room. Based on this change in the electronic medical records, the manager 102 could generate a group that receives messages related to this patient. The manager 102 could also detect a patient being admitted to the hospital, and based on this change in the medical records, the manager 102 may create a different group.

Additionally, the manager 102 can terminate a group based on any of these factors. For example, when a patient is discharged from the hospital, the manager 102 can terminate all groups associated with that patient.

In a further example, a user may not actively claim a role/group. Instead, the manager 102 can automatically assign users to a role/group. For example, by walking to the surgery floor, Kristen (continuing from the example above) can be added to the role/group of Active Medical Personnel—Surgery department. She would then be able to receive messages sent to this role without actively adding herself to it. This automatic assignment could also be based on several other factors. As an additional example, Kristen may have worked with a certain patient in the past, and based on this association, Kristen is added to the Patient X group during certain events associated with that patient.

If the destination is not associated with a role/group in the network, the messaging protocol determines whether the destination is a personnel target. A role, as mentioned above, may be a title, a job position, a group, etc. An exemplary role is an on-call cardiologist, a chief of surgery, etc. Further, a group may be a plurality of roles/users that are combined to one group. If the destination is not a personnel target, an error is generated at block 307. If the destination is a personnel target, a message is generated to the personnel target at block 305.

If the destination is associated with a role/group in the network, the messaging protocol identifies, at block 304, the personnel target associated with the role/group and generates the message to the personnel target at block 305.

Figure 4:
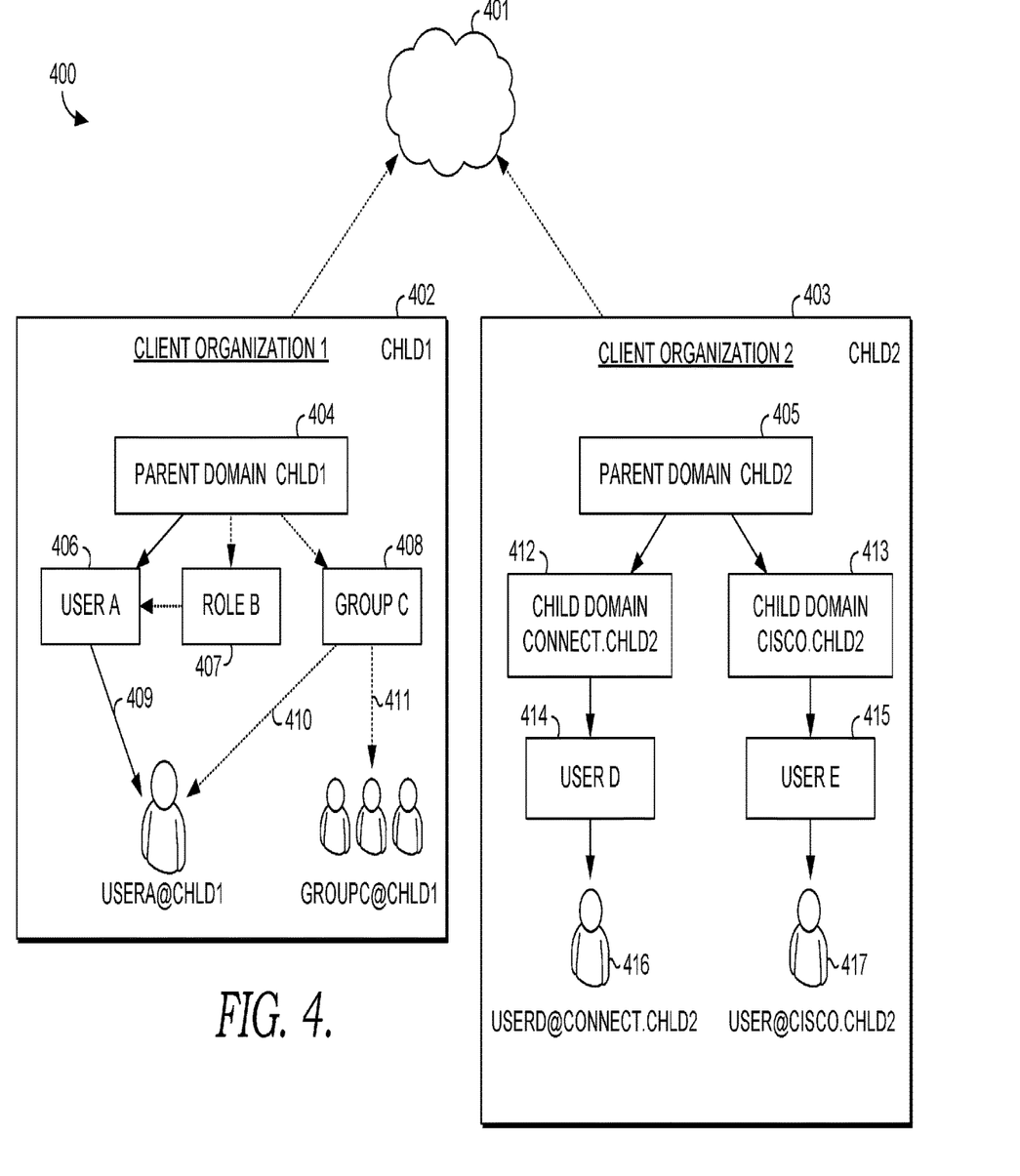
FIG. 4 is a block diagram of an exemplary computing environment suitable for use in implementations of the present disclosure.

FIG. 4 depicts an example between two different organizations. The system 400 includes a network 401 communicating with both client organization 1 402 and client organization 2 403. Each of client organization 1 402 and client organization 2 403 may be children of a parent domain. As shown in FIG. 4, client organization 1 402 includes a parent domain 404 of the client organization, user A 406, Role B 407 and Group C 408. Each of the user A 406, Role B 407, and Group C 408 are identifiable targets. A message may be received for Role B, for instance, and (as shown in FIG. 3) a personnel target associated with the role (e.g., User A 406) is identified and the message is communicated to the User A 406 at the address identified by the messaging protocol once the personnel target is identified. The same situation exists in client organization 2 where it is shown that the Parent domain 405 includes two child domains 412 and 413, each having users associated therewith such as User D 414 and User E 415. The parent domain 405 is in charge of each child domain and, thus, can receive a message for someone in either domain and communicate that message to targets within each domain. Furthermore, a child domain 413 could leverage an external protocol for which this invention can translate.

Additional embodiments allow the messaging protocol to extract data from various sources to intelligently route messages. For instance, presence information may be used in message communication. For example, if a message is sent to a nurse of an individual but that nurse recently logged off, the messaging protocol can re-route the message to an available party that is clinically relevant to the individual. Thus, the messaging protocol can leverage information in electronic medical records, clinical schedules, location services, presence, alternate databases, or other digitally accessible information for routing schemes.

As described above, implementations of the present disclosure relate to a design tool that facilitates generating user interface code for applications. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated by and is within the scope of the claims.

What is claimed is:

1. A computer system comprising:
a memory;
one or more processors; and
one or more computer storage media storing computer-useable instructions that, when used by the one or more processors, cause the one or more processors to:
detect a request to transmit a message including clinically relevant information identified from one or more electronic medical records to a destination, wherein the destination is within a separate domain and a target endpoint address of the destination is unknown;
determine whether the destination is associated with a role;
upon determining the destination is associated with a role, identify an intended target associated with the role;
generate a first transmission for the intended target without the target endpoint address;
identify a presence of a delay criteria for the intended target associated with the role;
identify at least one delivery identifier associated with the first transmission indicating that the first transmission can be delayed;
based on the presence of the delay criteria and the at least one delivery identifier indicating that the first transmission can be delayed, delay the first transmission; and
upon expiration of the predetermined time period, identify the absence of the delay criteria.

2. The computer system of claim 1, wherein, based on the absence of the delay criteria, the first transmission is communicated to the intended target.

3. The computer system of claim 2, wherein the first transmission includes a reminder option.

4. The computer system of claim 3, wherein the reminder option is a selectable option for selection by the user.

5. The computer system of claim 4, receiving a selection of the reminder option.

6. The computer system of claim 5, further comprising, upon receiving a selection of the reminder option, delaying the first transmission in accordance with a time period associated with the reminder option.

7. A method comprising:
detecting a request to transmit a message including clinically relevant information identified from one or more electronic medical records to a destination, wherein the destination is within a separate domain and a target endpoint address of the destination is unknown;
determining whether the destination is associated with a role;
upon determining the destination is associated with a role, identifying an intended target associated with the role;
generating a first transmission for the intended target without the target endpoint address;
identifying a presence of a delay criteria for the intended target associated with the role;
identifying at least one delivery identifier associated with the first transmission indicating that the first transmission can be delayed;
based on the presence of the delay criteria and the at least one delivery identifier indicating that the first transmission can be delayed, delaying the first transmission; and
upon expiration of the predetermined time period, identifying the absence of the delay criteria.

8. The method of claim 7, wherein, based on the absence of the delay criteria, the first transmission is communicated to the intended target.

9. The method of claim 8, wherein the first transmission includes a reminder option.

10. The method of claim 9, wherein the reminder option is a selectable option for selection by the user.

11. The method of claim 10, receiving a selection of the reminder option.

12. The method of claim 11, further comprising, upon receiving a selection of the reminder option, delaying the first transmission in accordance with a time period associated with the reminder option.

13. One more non-transitory computer-readable media having computer-executable instructions embodied thereon that, when executed, perform a method, the media comprising:
detecting a request to transmit a message including clinically relevant information identified from one or more electronic medical records to a destination, wherein the destination is within a separate domain and a target endpoint address of the destination is unknown;
determining whether the destination is associated with a role;
upon determining the destination is associated with a role, identifying an intended target associated with the role;
generating a first transmission for the intended target without the target endpoint address;
identifying a presence of a delay criteria for the intended target associated with the role;
identifying at least one delivery identifier associated with the first transmission indicating that the first transmission can be delayed;
based on the presence of the delay criteria and the at least one delivery identifier indicating that the first transmission can be delayed, delaying the first transmission; and
upon expiration of the predetermined time period, identifying the absence of the delay criteria.

14. The non-transitory computer-readable media of claim 13, wherein, based on the absence of the delay criteria, the first transmission is communicated to the intended target.

15. The non-transitory computer-readable media of claim 14, wherein the first transmission includes a reminder option.

16. The non-transitory computer-readable media of claim 15, wherein the reminder option is a selectable option for selection by the user.

17. The non-transitory computer-readable media of claim 16, receiving a selection of the reminder option.

18. The non-transitory computer-readable media of claim 17, further comprising, upon receiving a selection of the reminder option, delaying the first transmission in accordance with a time period associated with the reminder option.

* * * * *